(12) United States Patent
Lee et al.

(10) Patent No.: US 12,144,676 B2
(45) Date of Patent: Nov. 19, 2024

(54) SYSTEM AND METHOD FOR PROVIDING DEEP LEARNING-BASED VIRTUAL REALITY 3D EMBRYO MODEL

(71) Applicant: GIRJAESOFT CO., LTD., Seoul (KR)

(72) Inventors: Sang Lim Lee, Seoul (KR); Hyoung Jin Kim, Seoul (KR)

(*) Notice: Subject to any disclaimer, the term of this patent is extended or adjusted under 35 U.S.C. 154(b) by 934 days.

(21) Appl. No.: 17/271,032

(22) PCT Filed: Aug. 28, 2019

(86) PCT No.: PCT/KR2019/011011
§ 371 (c)(1),
(2) Date: Feb. 24, 2021

(87) PCT Pub. No.: WO2020/045987
PCT Pub. Date: Mar. 5, 2020

(65) Prior Publication Data
US 2021/0315539 A1 Oct. 14, 2021

(30) Foreign Application Priority Data

Aug. 31, 2018 (KR) .................. 10-2018-0103412
Jan. 21, 2019 (KR) .................. 10-2019-0007744

(51) Int. Cl.
*A61B 8/08* (2006.01)
*G06N 20/00* (2019.01)
(Continued)

(52) U.S. Cl.
CPC .......... *A61B 8/0866* (2013.01); *A61B 8/5207* (2013.01); *G06N 20/00* (2019.01);
(Continued)

(58) Field of Classification Search
None
See application file for complete search history.

(56) References Cited

U.S. PATENT DOCUMENTS

2017/0251999 A1* 9/2017 Noguchi .................. A61B 8/13
2019/0114462 A1* 4/2019 Jang ........................ G06N 3/084
(Continued)

FOREIGN PATENT DOCUMENTS

JP 2016-083192 A 5/2016
KR 10-2007-0058070 6/2007
(Continued)

OTHER PUBLICATIONS

KR-10-2010-040557A English Translation (Year: 2010).*
(Continued)

*Primary Examiner* — Miya J Cato
(74) *Attorney, Agent, or Firm* — ANTONIO HA & U.S. PATENT, LLC (57) ABSTRACT

The present invention discloses a virtual reality embryo image providing system. More specifically, the present invention relates to a deep learning-based embryo image providing system which extracts facial features of an embryo from an ultrasound image on the basis of a deep learning technique, generates a 3D model corresponding to the ultrasound image reflecting the facial features, and provides a virtual reality image using the 3D model. According to an embodiment of the present invention, the figure of an embryo can be displayed three-dimensionally through an HMD or the like by setting a plurality of codewords reflecting the features of each body part for a 2D embryo image, and performing a learning procedure on the basis of the codewords according to a deep learning model to provide a 3D model generated by combining the body components that are most similar to the actual face of the embryo. Therefore, a differentiated and realistic embryo imaging service can be provided to a pregnant person.

7 Claims, 8 Drawing Sheets

(51) Int. Cl.
*G06T 5/70* (2024.01)
*G06T 17/20* (2006.01)
*G06T 19/00* (2011.01)

(52) U.S. Cl.
CPC ............... *G06T 5/70* (2024.01); *G06T 17/20* (2013.01); *G06T 19/006* (2013.01); *A61B 2503/02* (2013.01); *G06T 2207/10132* (2013.01); *G06T 2207/20081* (2013.01); *G06T 2207/30201* (2013.01)

(56) References Cited

U.S. PATENT DOCUMENTS

2020/0134825 A1* 4/2020 Li .................. G06N 3/045
2021/0177374 A1* 6/2021 Balicki ............ G16H 10/20

FOREIGN PATENT DOCUMENTS

| KR | 10-2010-0040557 | | 4/2010 | |
| KR | 2010040557 A | * | 4/2010 | ............ G06T 15/04 |
| KR | 10-2013-0112127 | | 10/2013 | |
| KR | 10-2015-0108701 | | 9/2015 | |
| KR | 2015108701 A | * | 9/2015 | ........... A61B 8/0825 |
| KR | 10-2016-0115366 | | 10/2016 | |
| KR | 2016115366 A | * | 10/2016 | ....... G06K 19/06009 |
| KR | 2020109879 A | * | 9/2020 | |

OTHER PUBLICATIONS

KR-10-2015-108701A English Translation (Year: 2015).*
KR-10-2016-115366A English Translation (Year: 2016).*
Araceli Morales, Gemma Piella, Oriol Martinez, Federico M. Sukno, A quantitative comparison of methods for 3D face reconstruction from 2D images, 2018, 13th IEEE International Conference on Automatic Face & Gesture Recognition (Year: 2018).*
KR-10-2020-109879A English Translation (Year: 2020).*
English Specification of 10-2010-0040557.
English Specification of 10-2015-0108701.
English Specification of 10-2016-0115366.
English Specification of 10-2007-0058070.
English Specification of JP2016-083192A.
English Specification of 10-2013-0112127.

* cited by examiner

SYSTEM AND METHOD FOR PROVIDING DEEP LEARNING-BASED VIRTUAL REALITY 3D EMBRYO MODEL

TECHNICAL FIELD

The present invention relates to a system for providing a virtual reality 3D fetal model, and in particular, a system for providing a 3D fetal model based on deep learning that extracts facial features of a fetus based on deep learning technology on an ultrasound image, generates a 3D model reflecting the facial features, and provides virtual reality content using the same.

BACKGROUND ART

Currently, fetal ultrasound images are typically 2D flat images, and are used only for viewing purposes, e.g., by being directly viewed through the monitor by the pregnant woman or being stored in video format. Most of the conventional maternal apps and related services only provide information on pregnancy and childcare, or simply play video services. It is believed that this is due to the fact that technical development or service enhancement in related fields has not yet been made, and killer applications are insufficient.

Technologies for effectively visualizing fetal ultrasound images, especially 3D fetal faces, may be an important factor for enhancing related medical services. However, unlike conventional facial recognition targeting general facial images, image processing targeting the fetal face of an ultrasound image is extremely hard. This is because, by the nature of the ultrasound fetal face image, such features as eyes, nose, and mouth are unclear, and there are various variables depending on the location of the tissue in the uterus of the pregnant woman or the fetal face.

Accordingly, it is not an easy task to read the 2D image and apply depth information then convert it into a 3D stereoscopic image, and a difficulty exists in implementing such a service as to provide 3D fetal ultrasound images through a virtual reality display means, e.g., head-mounted display (HMD).

Prior art documents in the technical field to which the present invention pertains include Korean Patent Application Publication No. 10-2013-0112127.

DETAILED DESCRIPTION OF THE INVENTION

Technical Problems

The present invention was conceived to solve the foregoing problems, and the present invention aims to implement a fetal image similar to the actual fetal face on a virtual reality device by extracting features corresponding to the actual fetal face and generating a 3D fetal model reflecting the extracted features.

Means to Address Problems

To achieve the foregoing objects, according to an embodiment of the present invention, a system for providing a virtual reality 3D fetal model based on deep learning may comprise an image providing server generating a 3D model by analyzing a fetal image provided from a mobile terminal. The image providing server may include an image receiving unit receiving a fetal image and ROI information from the mobile terminal, an image processor inputting a fetal image corresponding to the ROI information to a deep learning model and extracting per-facial portion features, and a 3D model generator generating a 3D fetal model reflecting the per-facial portion features by selecting and synthesizing part models according to the per-facial portion features.

The image processor may include a preprocessor designating one or more frames from the input fetal image and removing noise; and an ROI matching unit determining a facial area, as a target for modeling, by matching the ROI information onto the frame.

The image receiving unit may receive a codeword for a similar model composed of a plurality of components selected from the mobile terminal along with reception of the fetal image and the ROI information. The image processor may include a deep learning model for performing a machine learning process using the codeword corresponding to the plurality of components, as training data, or extracting a facial feature codeword for an input image after training.

The facial area may include one or more of an eye, a nose, a mouth, and a face. The codeword may be a code resultant from a shape of the facial area in a binary format.

The image processor may include a component selector exchanging one or more components for each facial area included in an existing 3D model, corresponding to the codeword.

The image providing server may include a member management unit determining whether a user is registered as a member according to login information input from the mobile terminal and performing a login process. The image processor may store the fetal image in storage allocated to a user identified by the member management unit and extract the stored 3D fetal image.

The image processor may receive growth information including a pregnancy period and growth parameter for a pregnant woman from the mobile terminal. The 3D model generator may store the generated 3D model in a database according to the growth parameter per pregnancy period.

The mobile terminal may include a communication unit connected to an information communication network to communicate with an external system, a storage device storing the fetal image transmitted from an ultrasound diagnosis device through the communication unit, an ROI setting unit receiving a selection of a facial area in the fetal image according to a user input and setting the facial area as the ROI information, a growth information input unit receiving growth information including a pregnancy period and growth parameter for a pregnant woman, a terminal library DB storing a library in which components corresponding to a plurality of face shapes are defined, and a feedback unit receiving a selection of one or more components for facial portion of the fetus from a user and transmitting a codeword of a similar model to the image providing server.

To achieve the foregoing objects, according to another embodiment of the present invention, a method for providing a model by an image providing server of a deep learning-based virtual reality 3D fetal model providing system may comprise receiving a fetal image and ROI information from a mobile terminal, extracting per-facial portion features by inputting a fetal image corresponding to the ROI information to a deep learning model, generating a 3D fetal image reflecting the per-facial portion features through 3D modeling, and providing the 3D fetal image to the mobile terminal.

The method may further comprise, after providing the 3D fetal image to the mobile terminal, receiving a codeword for a similar model including one or more components per facial portion of the fetus selected by a user from the mobile terminal and performing a machine learning process on the deep learning model using the codeword as training data.

Advantageous Effects

According to an embodiment of the present invention, a plurality of codewords in which features are reflected for each body part of a 3D fetal image are set and, based thereupon, a learning process is performed according to a deep learning model to thereby provide a 3D model generated with a combination of body components most similar to the actual fetal face. Therefore, the appearance of the fetus may be stereoscopically displayed through, e.g., an HMD, thereby providing a differentiated and realistic fetal image service to pregnant women.

Further, the fetal imaging service according to an embodiment of the present invention may be used in health care applications for fetuses and pregnant women, such as prenatal care and depression treatment for pregnant women.

MODE TO PRACTICE THE INVENTION

Throughout the specification, when an element "includes" another element, the element may further include the other element, rather excluding the other element, unless particularly stated otherwise. Further, the term "unit," "device," or "system" as used herein denote a unit processing at least one function or operation and be implemented in hardware, software, or a combination thereof.

Although some exemplary embodiments of the disclosure are described herein, the technical spirit or scope of the disclosure are not limited thereto. Prior to going into the detailed description of the disclosure, it might be effective to define particular words and phrases as used herein. As used herein, the terms "include" and "comprise" and their derivatives may mean doing so without any limitations. As used herein, the term "or" may mean "and/or." As used herein, the phrase "associated with" and "associated therewith" and their derivatives may mean "include," "be included within," "interconnect with," "contain," "be contained within," "connect to or with," "couple to or with," "be communicable with," "cooperate with," "interleave," "juxtapose," "be proximate to," "be bound to or with," "have," or "have a property of." As used herein, the term "controller" may mean any device, system, or part thereof controlling at least one operation. As used herein, the term "device" may be implemented in hardware, firmware, software, or some combinations of at least two thereof.

Various schemes or methods described herein may be implemented in hardware, software, or a combination thereof. As used herein, the term "unit," "device," or "system" may also be equivalent to a computer-related entity, a hardware component, a software component, or a combination thereof. Each function executed in the system of the present invention may be configured as a module unit and may be recorded in one physical memory or be distributed and recorded between two or more memories and recording media.

Hereinafter, a deep learning-based virtual reality 3D fetal model providing system and method according to an embodiment of the present invention is described with reference to the drawings.

Figure 1:
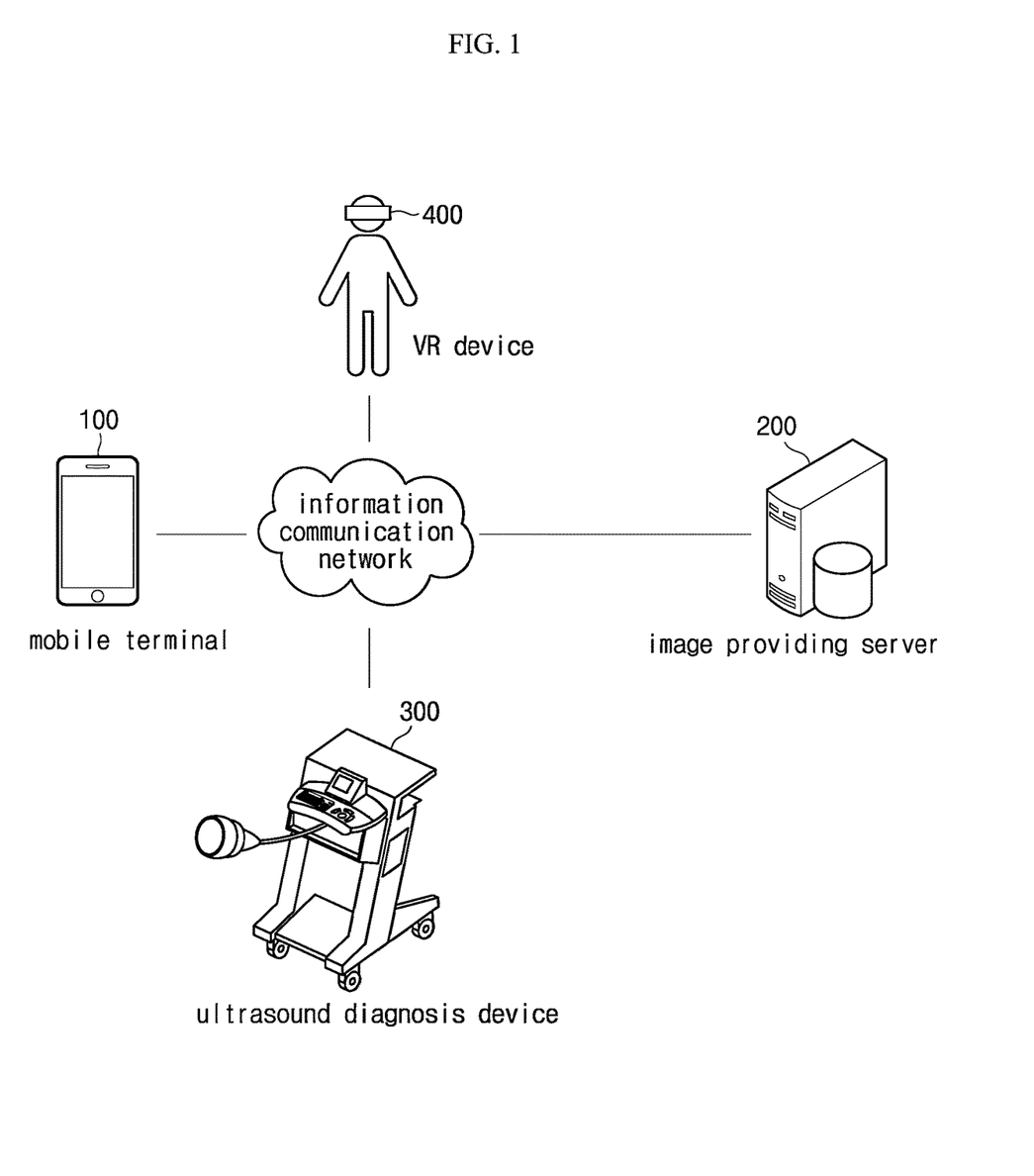
FIG. 1 is a view schematically illustrating an overall configuration of a deep learning-based virtual reality 3D fetal model providing system according to an embodiment of the present invention.

FIG. 1 is a view schematically illustrating an overall configuration of a deep learning-based virtual reality 3D fetal model providing system according to an embodiment of the present invention.

Referring to FIG. 1, a deep learning-based virtual reality 3D fetal model providing system according to an embodiment of the present invention may include a user's mobile terminal 100, an image providing server 200 that interworks with the mobile terminal 100 to convert a 3D fetal image into a 3D model using a trained deep learning model, an ultrasound diagnosis device 300 that photographs a pregnant woman and provides the 2D fetal image to the mobile terminal 100, and a VR device 400 implemented as, e.g., an HMD to display the 3D model as a virtual reality image.

The mobile terminal 100 is a terminal that is possessed by the user, such as a pregnant woman or her guardian and is connected to the image providing server 200 through an information communication network to transmit the fetal image stored in the terminal to the image providing server 200 to thereby request a 3D model for the fetal image.

As the user desires to view a more realistic image of the fetus with the VR device 400, the user may transmit her fetal image stored in her mobile terminal 100 to the image providing server 200 through the information communication network.

To that end, the mobile terminal 100 previously needs to receive and store a 2D original fetal image from the ultrasound diagnosis device 300 through wired or wireless communication.

Further, upon transmitting the fetal image, the mobile terminal 100 further receives, and transmits together with the fetal image, growth information including what week of pregnancy or growth parameters of the pregnant woman, thereby receiving the 3D model updated according to the degree of growth of the fetus from the image providing server 200.

As the mobile terminal 100, a smartphone or tablet PC may be used which includes a communication module, microprocessor, memory and storage that may store and execute an application program capable of interworking with the image providing server 200.

The image providing server 200 may interwork with a plurality of mobile terminals 100 through the information communication network and store fetal images transmitted from each mobile terminal 100 and may use the fetal images as data for machine learning. Further, the image providing server 200 may separate parts of the fetus's face into, e.g., eyes, nose, and mouth and designating features of the face shape, extract the most similar components through comparison with a model library accumulated in the database, determine a 3D model corresponding to the fetal face through a combination of the components, and provide the determined 3D model, as a 3D fetal image, to the mobile terminal 100.

As the image providing server 200, a server device equipped with a high-performance microprocessor and high-capacity memory and storage may be used that may process, without delay, the tasks of performing machine learning on the fetal images transmitted from the multiple mobile terminal 100, generating and providing a 3D model, and updating the 3D model according to the growth of the fetus.

The ultrasound diagnosis device 300 may include a predetermined probe to obtain acquire an ultrasound image, which is an original image of a 3D model, for the diagnosis target.

Further, the ultrasound diagnosis device 300 may transmit the ultrasound image to the mobile terminal through a short-range wireless communication network using a communication module included in the ultrasound diagnosis device 300, so that the original fetal image may be displayed and stored in real-time.

The VR device 400 may be wiredly or wirelessly connected to the image providing server 200 to reproduce the 3D fetal image provided by the mobile terminal 100. As the VR device 400, a head-mounted device equipped with, e.g., a geomagnetic sensor or an acceleration sensor, as well as a display, may be used, and may implement a stereoscopic image for the fetus corresponding to the direction in which the user views the diagnosis target.

Further, the VR device 400 may be configured as a housing member in which a predetermined reproducing terminal capable of reproducing the virtual reality image is installed, and be implemented with a structure of having the mobile terminal 100 mounted thereon to produce the 3D fetal image.

According to the above-described structure, the deep learning-based virtual reality 3D fetal model providing system according to an embodiment of the present invention may provide the original fetal image acquired through the ultrasound diagnosis device to the image providing server through the information communication network, generate a 3D fetal model according to a modeling process to which a deep learning scheme is applied, and display the 3D fetal model through the VR device, thereby providing the 3D fetal model which is closer to the actual appearance.

Hereinafter, the mobile terminal of the deep learning-based virtual reality 3D fetal model providing system is described with reference to the drawings.

Figure 2:
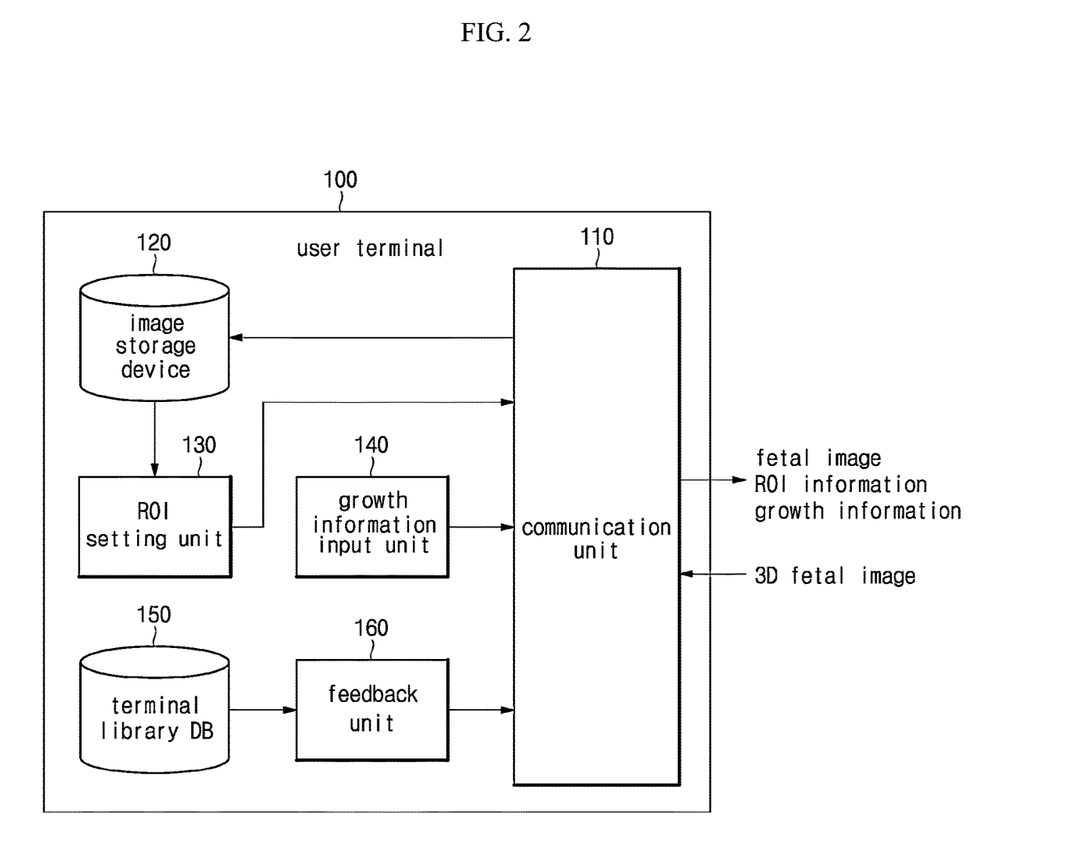
FIG. 2 is a view illustrating a structure of a mobile terminal of a deep learning-based virtual reality 3D fetal model providing system according to an embodiment of the present invention.

FIG. 2 is a view illustrating a structure of a mobile terminal of a deep learning-based virtual reality 3D fetal model providing system according to an embodiment of the present invention. In the following description, each component constituting the mobile terminal may be implemented as an application program executable by a predetermined microprocessor and recorded in a recording medium.

Referring to FIG. 2, the mobile terminal 100 of the present invention may include a communication unit 110 connected to an information communication network to transmit/receive data with an external system, an image storage device 120 storing fetal images transmitted from an ultrasound diagnosis device through the communication unit 110, an ROI setting unit 130 receiving a selection of a facial area in the fetal image according to the user's input and setting the same as ROI information, a growth information input unit 140 receiving growth information including the pregnancy term and growth parameters of the pregnant woman, a terminal library DB 150 storing a library in which components corresponding to a plurality of facial shapes are defined, and a feedback unit 160 receiving one or more components for each facial portion of the fetus from the user and transmitting a codeword of a similar model to the image providing server.

The communication unit 110 may connect to the information communication network to transmit/receive data to and from an external system. The communication unit 110 may receive an original fetal image from the ultrasound diagnosis device, provide an original fetal image for which an ROI has been set to the image providing server, or receive a 3D fetal image from the image providing server.

The image storage device 120 may store original fetal images transmitted from the ultrasound diagnosis device and 3D fetal images provided from the image providing server. In particular, as fetal images are classified and stored by date, the user may easily identify changes in the fetus from the past to the present. The 3D fetal image stored in the image storage device may be reproduced on the mobile terminal 100 or transmitted to an external VR device to be reproduced in the form of a stereoscopic image.

The ROI setting unit 130 may provide an interface through which the user may set a region of interest (ROI) for the fetal image through region selection. The user, e.g., the pregnant woman or her guardian, may designate an ROI through such an action as dragging the area corresponding to the fetus's face in the original fetal image displayed through the screen of the mobile terminal 100, and the ROI setting unit 130 may generate ROI information for the corresponding fetal image.

The growth information input unit 140 may receive growth information for the ROI-set fetal image. In addition to uploading the fetal image and ROI information, the user may input, as the growth information, the time of photographing the currently uploaded fetal image, that is, the pregnancy term, and various information related to the growth of the fetus.

The fetal image, ROI information, and growth information may be synchronized and transmitted to the image providing system through the communication unit 110. Accordingly, the image providing system performs a 3D modeling process using the gathered data and generates a 3D fetal model of the fetus.

The terminal library DB 150 may store various types of 3D components corresponding to each part of the fetus's face.

The deep learning-based virtual reality 3D fetal model providing system according to an embodiment of the present invention is characterized by enhancing the performance of the deep learning model through user feedback. Accordingly, the user terminal 100 stores a number of 3D components, which are various types of models for each feature part, i.e., eyes, nose, mouth, and face, of the fetus's face, and the user may select the component most similar to the shape of her fetus from among the 3D components stored in the terminal library DB 150 and generate a similar face model and provide an image and codeword for the similar face model to the image providing server.

Accordingly, the image providing server may use the codeword of the fetus's similar face model provided from the user terminal 100, as training data of the deep learning model, thereby enhancing the accuracy of 3D modeling on the fetus.

The feedback unit 160 may extract 3D components for each facial portion stored in the terminal library DB 150 and provide an interface through which the user may make a designation. Further, when the components for the feature parts of the fetus's face are selected by the user, the feedback unit 160 generates a similar face model by combining the selected components and provide the codeword of the similar face model to the image providing server through the communication unit 110.

By the above-described structure, the mobile terminal according to the embodiment of the present invention may provide the fetal image to the image providing server and make a request for a 3D fetal model most similar to the actual fetus to the image providing server, and the mobile terminal may also feed back information on the similar face model, thereby maximizing the similarity in 3D modeling.

Hereinafter, the image providing server of the deep learning-based virtual reality 3D fetal model providing system is described with reference to the drawings.

Figure 3:
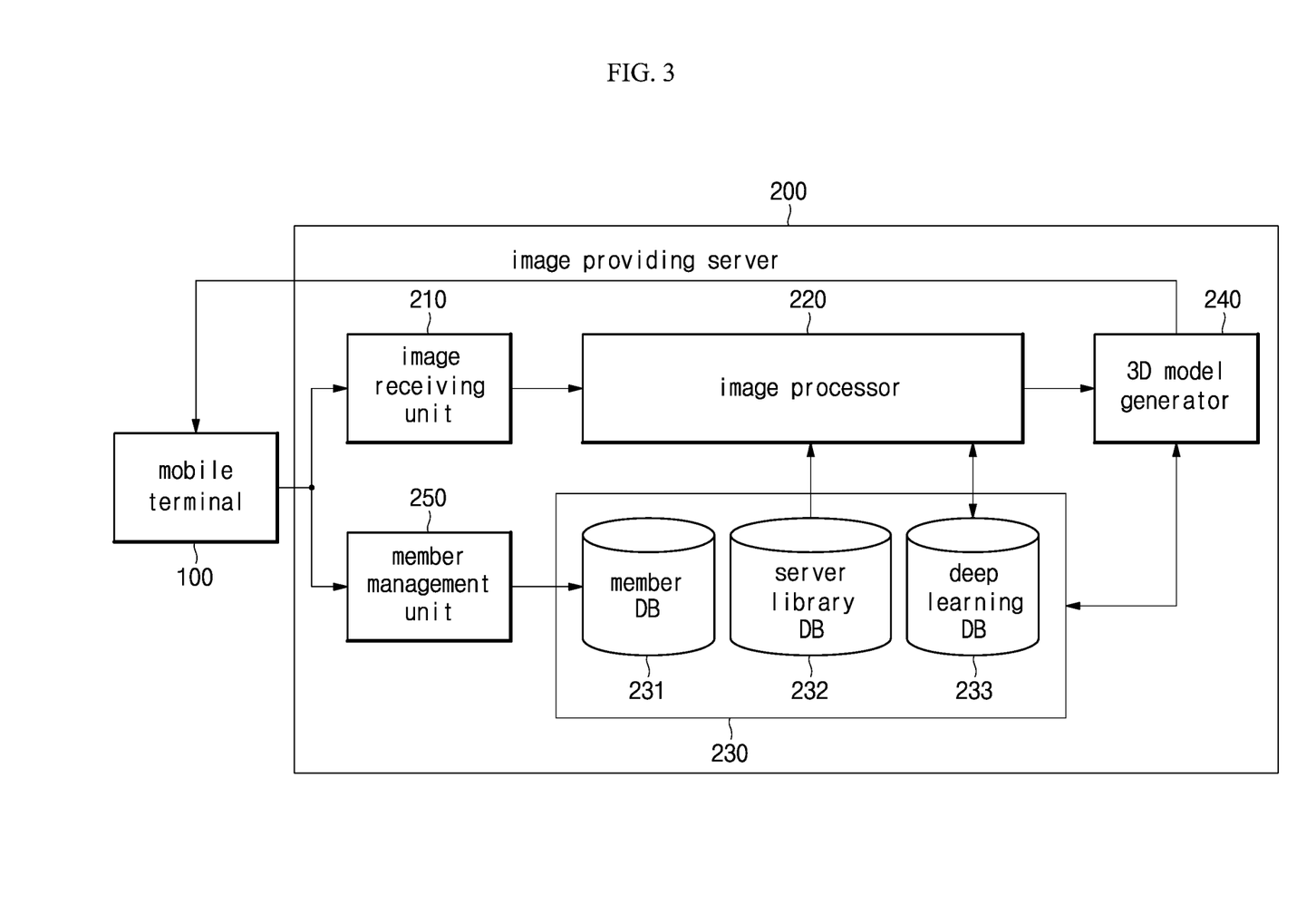
FIG. 3 is a view illustrating a structure of an image providing server of a deep learning-based virtual reality 3D fetal model providing system according to an embodiment of the present invention.
Figure 4:
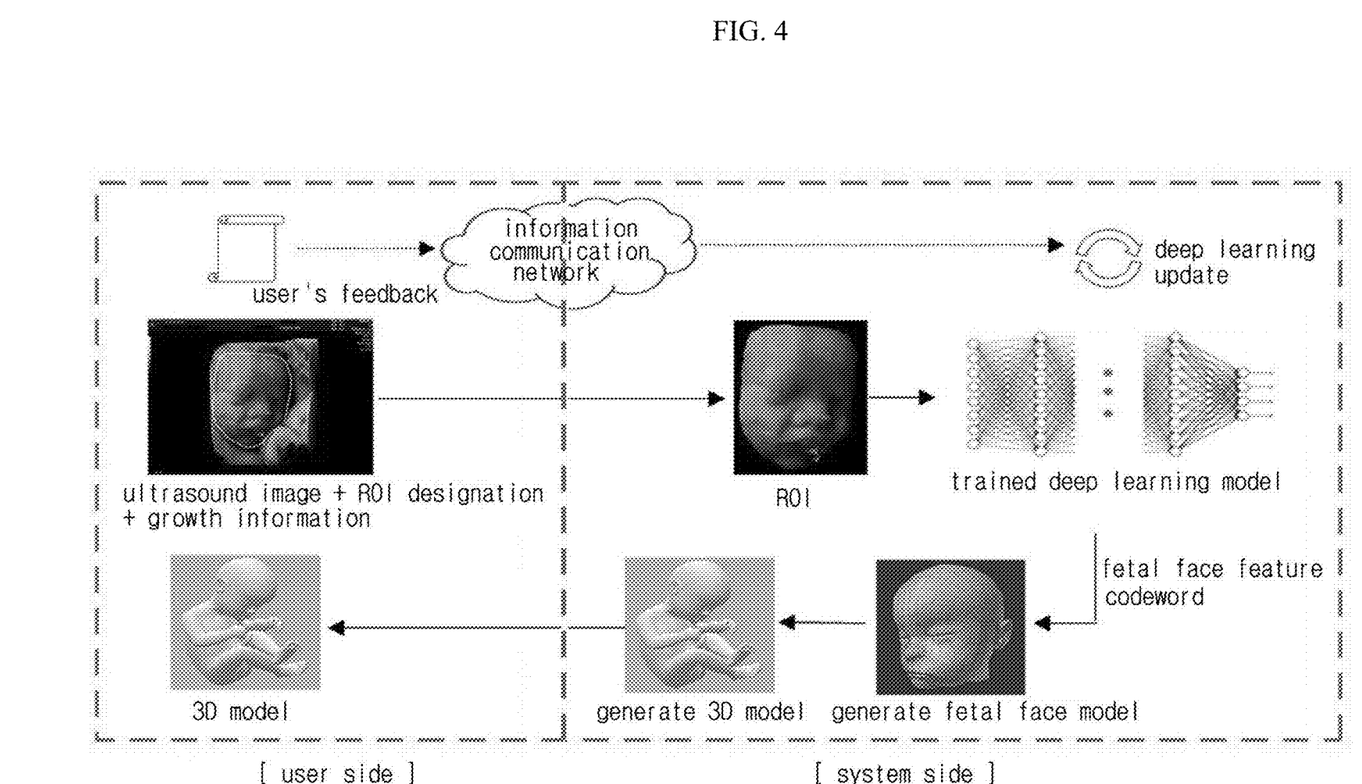
FIG. 4 is a view illustrating a process for increasing the matching accuracy of a 3D model by reflecting user feedback in a deep learning-based virtual reality 3D fetal model providing system according to an embodiment of the present invention.

FIG. 3 is a view illustrating a structure of an image providing server of a deep learning-based virtual reality 3D fetal model providing system according to an embodiment of the present invention, and FIG. 4 is a view illustrating a process for increasing the matching accuracy of a 3D model by reflecting user feedback in a deep learning-based virtual reality 3D fetal model providing system according to an embodiment of the present invention.

Referring to FIGS. 3 and 4, the image providing server 200 according to an embodiment of the present invention may include an image receiving unit 210 receiving a fetal image and ROI information from the mobile terminal 100, an image processor 220 inputting the fetal image corresponding to the ROI information to a deep learning model to thereby extract features per facial portion, a database 230 storing a server library to which the deep learning model refers, a 3D model generator 240 generating a 3D fetal model reflecting the per-facial portion features through 3D modeling, and a member management unit 250 determining whether a user is registered as a member according to login information entered from the mobile terminal 100 and performs a login process.

The image receiving unit 210 may receive original fetal images from one or more mobile terminals 100 through an information communication network. The image receiving unit 210 may interwork with an application program installed on the mobile terminal 100 to receive a 3D stereoscopic image for the fetus or to periodically receive fetal images from the user who intends to manage the fetal images according to the growth period of the fetus.

Here, the image receiving unit 210 receives the original fetal image, ROI information set in the original fetal image, and information on the current fetal growth period together, thereby enabling the appearance of the fetus for each growth period to be stored and managed.

The image processor 220 may generate a 3D fetal model for virtual reality by performing 3D modeling using the original fetal image received by the image receiving unit 210. The image processor 220 may extract facial portions of the fetus by referring to the ROI information in the original fetal image, and extract per-facial portion components most similar to each part of the face for 3D modeling.

The fetus's face in the 3D ultrasound fetal image look unclear for the eyes, nose, and mouth, and the facial portions may be blocked by floating materials in the womb or according to the fetus's position. Thus, a training model optimized for the fetal image is required, and the image processor 220 extracts per-facial portion components which exhibit the minimum error or difference from the actual face through a known deep learning model.

Further, the image processor 220 may increase the accuracy of matching of the 3D model by updating the deep learning model using the codeword of the similar face model, as feedback information transmitted from the mobile terminal 100, as training data for the deep learning model.

The database 230 may store various types of information for 3D modeling. In particular, the image processor 220 refers to the library for 3D modeling and requires a plurality of training data for the deep learning model. The database 230 may store various types of information necessary for such 3D modeling.

This database 230 may include a plurality of database systems logically or physically divided according to their purposes, and the database 230 may include a member DB 231 for storing member and fetal information and managing fetal images according to the growth period of the fetus 231, a server library DB 232 storing a library including components for each facial portion of the fetus, and a deep learning DB 233 storing training data used for machine learning.

The model generator 240 may update the face of a standard 3D fetal model by combining the plurality of per-facial portion components derived by the image processor 220.

The member management unit 250 may provide functions, such as a membership registration process, login process, and member information management of pregnant women or guardians who wish to use the 3D fetal images provided by the system of the present invention.

In particular, the user may access the image providing server 200 from time to time to manage and identify the image of the fetus for each pregnancy period stored in the storage allocated to his account, and the member management unit 250 may perform a login procedure according to a request from the mobile terminal 100 and identify the 3D fetal image for the user, stored in the storage of the database 230.

According to the above-described structure, the image providing server of the deep learning-based virtual reality 3D fetal model providing system according to an embodiment of the present invention may provide a 3D model for the fetal image provided by the user and continuously enhance the accuracy of machine learning through feedback from the user, thereby providing a more realistic fetal model.

Hereinafter, the image processor included in the image providing server according to an embodiment of the present invention is described with reference to the drawings.

Figure 5:
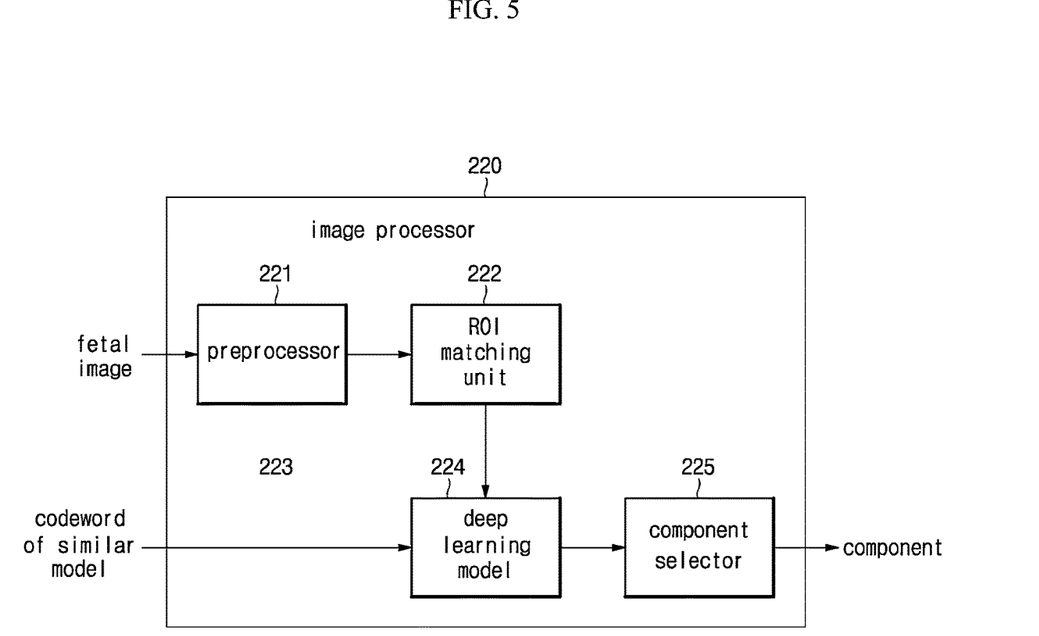
FIG. 5 is a view illustrating a structure of an image processor of an image providing server according to an embodiment of the present invention.
Figure 6:
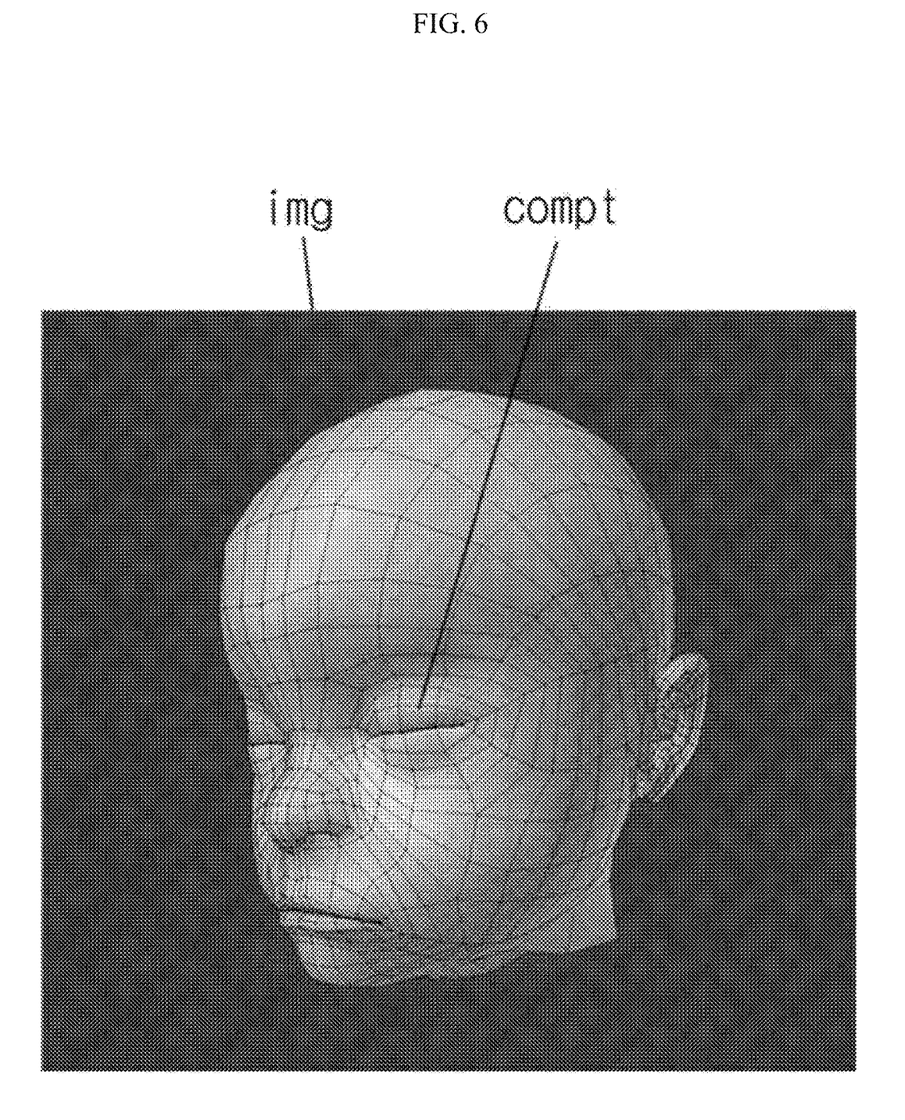
FIG. 6 is a view illustrating a 3D modeled image of an image providing server according to an embodiment of the present invention.

FIG. 5 is a view illustrating a structure of an image processor of an image providing server according to an embodiment of the present invention, and FIG. 6 is a view illustrating a 3D modeled image of an image providing server according to an embodiment of the present invention.

Referring to FIGS. 5 and 6, the image processor 220 according to an embodiment of the present invention may include a preprocessor 221 designating one or more frames in a received fetal image and removing noise, an ROI matching unit 222 determining a facial area which is a target for modeling by matching ROI information onto the frame, a deep learning model 224 for performing a machine learning process on the set deep learning model using the codewords corresponding to the plurality of components, as training data, or extracting facial feature codewords for the input image after training, and a component selector 225 exchanging one or more components per facial portion included in the existing 3D model, corresponding to the codeword.

The preprocessor 221 may designate a frame of a predetermined range to be subjected to 3D modeling according to settings, for the input fetal image, and may remove noise for the designated frame.

The ROI matching unit 222 may determine the facial portion by matching ROI information designated by the user onto the noise-removed frame. The ROI information may include coordinates for the facial area of the fetus selected by the user in the fetal image, and the ROI matching unit 222 may extract the image corresponding to the facial area through the ROI information.

The above-described components may be defined by classifying the shape of each facial portion in a predetermined number, and the components may be classified into three types for each facial portion as illustrated in Table 1 below.

TABLE 1

| Feature part | Classification criteria | Type 1 | Type 2 | Type 3 |
| --- | --- | --- | --- | --- |
| Eye shape | Degree of protrusion of eye area | sunken | normal | protruding |
| Nose shape | how high and broad | low and broad | normal | high |
| Mouth shape | degree of protrusion of upper/lower lips | upper protrusion | normal | lower protrusion |
| Face shape | degree of slimness of cheeks and chin | slim | normal | round |

Here, the shape of each facial portion may correspond to any one of the three types, and have a binary-format value designated thereto. As an example, if the eye shape is normal, then the codeword becomes '010', and if the face shape is slim, the codeword becomes '100'. The deep learning model 224 may receive the extracted codewords as training data and perform machine learning, and the per-facial portion feature information corresponding to the facial area of the fetal image by the ROI matching unit 222 is labeled, and training data is generated.

Specifically, the deep learning model 224 may operate in a learning mode or a feature extraction mode. When operating in the training mode, the deep learning model 224 uses a number of images input by the user and similar model codewords matching the images, for training. Here, the codeword of the similar model may be used only when learning based on user feedback.

Further, when operating in the feature extraction mode, the deep learning model 224 outputs the feature as the codeword based on the learned information if a fetal image is input.

To that end, image frames for training may be designated in the fetal image through the preprocessor 211 and the ROI matching unit 222, and ROI information for designating the fetus's facial area in the image area of each frame may be set, so that the facial area of the fetus in the ROI may be utilized as an input image for training. Since the 3D fetal image typically includes the fetus's movement, there is an advantage that a large number of images for training may be obtained from one video.

Here, to designate the feature of the fetus's facial portion, a feature designation function using a similar 3D model may be implemented. The face shape model most similar to the face shape, eyes, nose, and mouth in the facial area of the fetal image and a model for the facial portion may be selected from the library, so that a 3D face model overall closest to the face in the fetal image may be determined. To that end, various facial shapes and models for the facial portions are produced as components, and model selection and replacement, rotation or movement may be carried out for easy comparison with the fetal image.

Here, the generated images for training and the feature codewords for the fetus's face may be constructed as a learning database for integrated management thereof so as to facilitate addition or modification to the information later.

The component selector 225 may replace one or more components for each facial portion included in the existing 3D model, corresponding to the codeword, so that 3D modeling may be performed using the updated components upon generating a 3D fetal model.

According to the above-described structure, the image processor according to an embodiment of the present invention may provide components for generating a 3D fetal model, and may reflect feedback for a similar model provided from the user to the deep learning model 224. In this case, the component may be delivered in the form of a codeword.

Hereinafter, a deep learning-based virtual reality 3D fetal model providing method according to an embodiment of the present invention is described with reference to the drawings.

Figure 7:
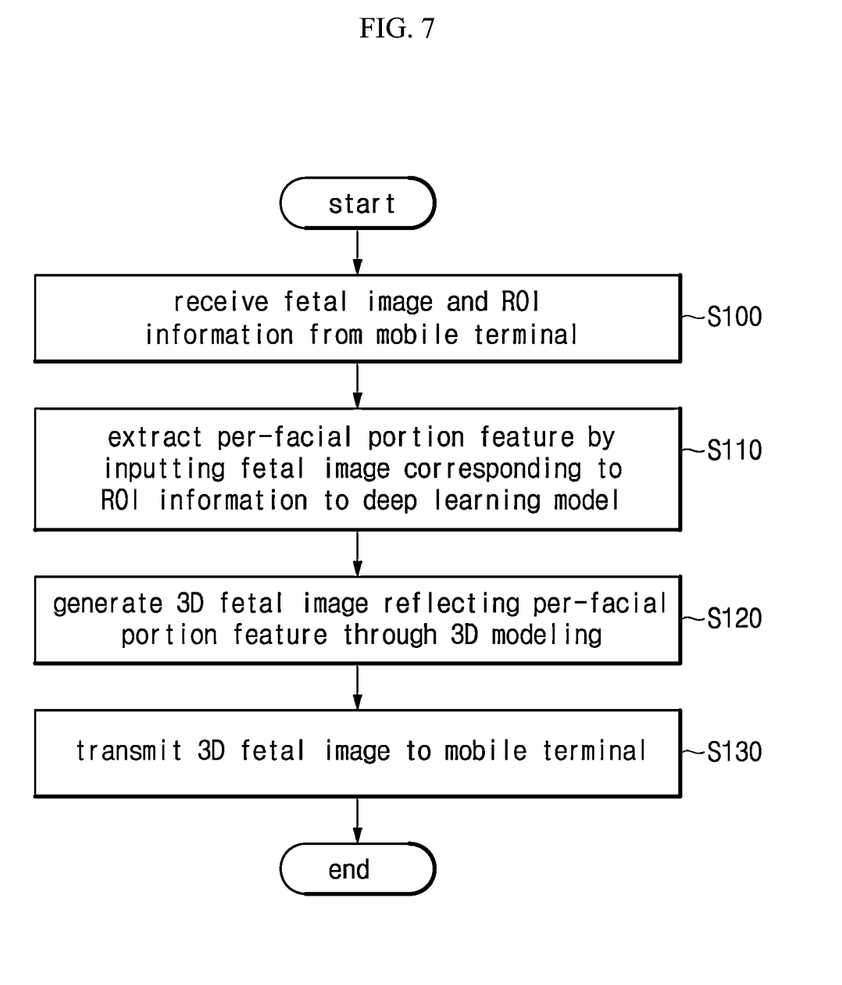
FIG. 7 is a view illustrating a method of providing a virtual reality 3D fetal model based on deep learning according to an embodiment of the present invention.

FIG. 7 is a view illustrating a method of providing a virtual reality 3D fetal model based on deep learning according to an embodiment of the present invention. Unless specifically stated, each step described below is performed by the above-described image providing server or its components.

Referring to FIG. 7, a method for providing a virtual reality 3D fetal model based on deep learning according to an embodiment of the present invention may include the step S100 of receiving a fetal image and ROI information from a mobile terminal, the step S110 of extracting per-facial portion features by inputting a fetal image corresponding to the ROI information to a deep learning model, the step S120 of generating a 3D fetal image reflecting the per-facial portion features through 3D modeling, and the step S130 of providing the 3D fetal image to the mobile terminal.

In the step S100 of receiving the fetal image and ROI information from the mobile terminal, the mobile terminal receives and stores an original fetal image of the fetus from the ultrasound diagnosis device, generates ROI information according to the user's designation, and transmits the ROI information along with the stored original fetal image to the image providing server.

In the step of extracting per-facial portion features by inputting the fetal image corresponding to the ROI information to the deep learning model, the image providing server extracts the facial area in the fetal image according to the image coordinates included in the ROI information, and extracts features for each portion in the facial area through the deep learning model.

In the step S120 of generating a 3D fetal model reflecting the per-facial portion features through 3D modeling, the deep learning model features the per-facial portion features and generates one 3D fetal model.

In the step S130 of providing the 3D fetal model to the mobile terminal, the image providing server provides the generated 3D fetal model to the mobile terminal.

Accordingly, the user may enjoy a stereoscopic fetal image at various viewpoints for the fetus through the mobile terminal, and may also enjoy a 3D fetal model in a virtual reality manner through a VR device interworking with the mobile terminal.

As steps for the user's feedback to enhance the performance of the deep learning model after step S130, the method may further include the step of receiving a codeword for a similar model including one or more components for each facial portion of the fetus selected by the user from the mobile terminal and the step of performing a machine learning process on the deep learning model using the codeword as training data, after providing the 3D fetal image to the mobile terminal.

Hereinafter, the technical spirit of the present invention is described through a deep learning process by a deep learning-based virtual reality fetal image providing system according to an embodiment of the present invention and a process of extracting a codeword in the process.

Figure 8:
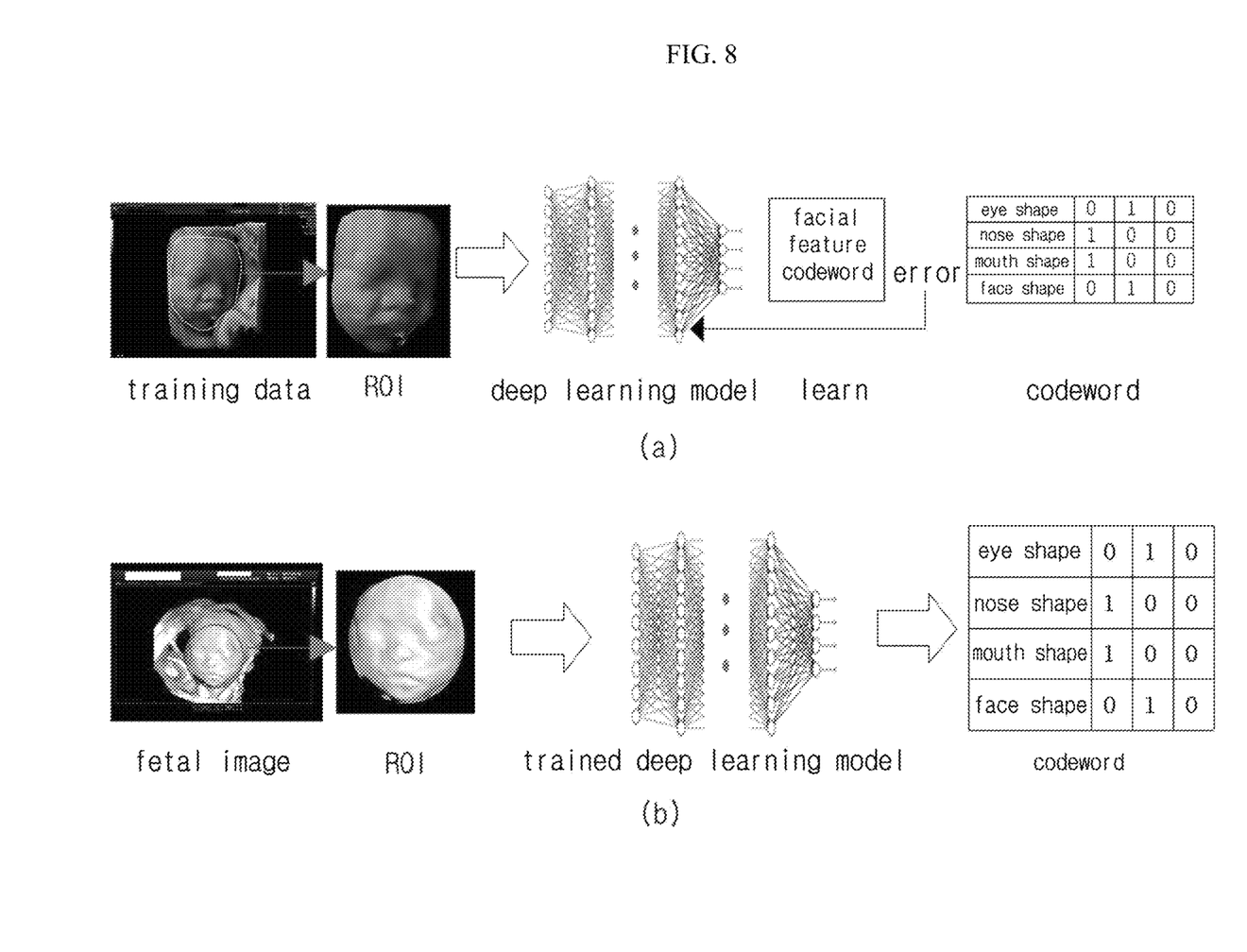
FIG. 8 is a view schematically illustrating a deep learning process (a) in a deep learning-based virtual reality 3D fetal model providing system according to an embodiment of the present invention and a codeword extraction process (b) using the learned deep learning model.

FIG. 8 is a view schematically illustrating a deep learning and codeword extraction process of a deep learning-based virtual reality fetal image providing system according to an embodiment of the present invention.

Referring to FIG. 8, the deep learning-based virtual reality fetal image providing system according to an embodiment of the present invention is configured to use various fetal images as training data, prepare an image for each fetus, designate ROI information corresponding to the face in the image, and apply the same to the deep learning model to thereby perform 3D modeling.

To train the deep learning model, a number of training images and codewords reflecting the facial features of the images are previously defined, and the deep learning model training process is performed. The training process is a process of optimizing the deep learning model to reduce errors so that a predefined image and a codeword matching thereto are output (a).

Here, as binarized data, identification and extraction of a component may be performed via a codeword corresponding thereto.

Accordingly, if the user provides the current fetal image and ROI information, the codeword of the component corresponding to each facial portion is extracted and a 3D model is generated through the learned deep learning model reflecting the user's feedback (b).

According to an embodiment of the present invention, it is possible to reduce errors and enhance the quality of the 3D model by updating training data of the deep learning model according to the user's feedback.

To that end, if a library including a plurality of components is provided to the user's mobile terminal, and a similar model is generated by the user's selection of the most similar components from the per-facial portion components provided from the library, and a codeword is provided, the image providing server uses the same as training data.

While the disclosure has been shown and described with reference to exemplary embodiments thereof, it will be apparent to those of ordinary skill in the art that various changes in form and detail may be made thereto without departing from the spirit and scope of the disclosure as defined by the following claims. Accordingly, the scope of the disclosure should be defined by the following claims and equivalents thereof, but not by the above-described embodiments.

| * Legend of reference numbers * | |
| --- | --- |
| 100: mobile terminal | 110: communication unit |
| 120: image storage device | 130: ROI setting unit |
| 140: growth information input unit | 150: terminal library DB |
| 160: feedback unit | 200: image providing server |
| 210: image receiving unit | 220: image processor |
| 221: preprocessor | 222: ROI matching unit |
| 224: deep learning model | 225: component selector |
| 230: database | 240: 3D model generator |
| 250: member management unit | 300: ultrasound diagnosis device |
| 400: VR device | |

The invention claimed is:

1. A system for providing a virtual reality 3D fetal model based on deep learning, the system comprising an image providing server generating a 3D model by analyzing a fetal image provided from a mobile terminal, the image providing server including:
    an image receiving unit receiving a fetal image and ROI information from the mobile terminal;
    an image processor inputting a fetal image corresponding to the ROI information to a deep learning model and extracting per-facial portion features; and
    a 3D model generator generating a 3D fetal model reflecting the per-facial portion features by selecting and synthesizing part models according to the per-facial portion features, wherein the image processor includes:
    a preprocessor designating one or more frames from the input fetal image and removing noise; and
    an ROI matching unit determining a facial area, as a target for modeling, by matching the ROI information onto the frame, wherein the image receiving unit receives a codeword for a similar model composed of a plurality of components selected from the mobile terminal along with reception of the fetal image and the ROI information, and wherein the image processor includes a deep learning model for performing a machine learning process using the codeword corresponding to the plurality of components, as training data, or extracting a facial feature codeword for an input image after training.

2. The system of claim 1, wherein the facial area includes one or more of an eye, a nose, a mouth, and a face, and wherein the codeword is a code resultant from a shape of the facial area in a binary format.

3. The system of claim 2, wherein the image processor includes a component selector exchanging one or more components for each facial area included in an existing 3D model, corresponding to the codeword.

4. The system of claim 1, wherein the image providing server includes a member management unit determining whether a user is registered as a member according to login information input from the mobile terminal and performing a login process, and wherein the image processor stores the fetal image in storage allocated to a user identified by the member management unit and extracts the stored 3D fetal image.

5. The system of claim 1, wherein the image processor receives growth information including a pregnancy period and growth parameter for a pregnant woman from the mobile terminal, and wherein the 3D model generator stores the generated 3D model in a database according to the growth parameter per pregnancy period.

6. A system for providing a virtual reality 3D fetal model based on deep learning, the system comprising an image providing server generating a 3D model by analyzing a fetal image provided from a mobile terminal, the image providing server including:
- an image receiving unit receiving a fetal image and ROI information from the mobile terminal;
- an image processor inputting a fetal image corresponding to the ROI information to a deep learning model and extracting per-facial portion features; and
- a 3D model generator generating a 3D fetal model reflecting the per-facial portion features by selecting and synthesizing part models according to the per-facial portion features, wherein the mobile terminal includes:
- a communication unit connected to an information communication network to communicate with an external system;
- a storage device storing the fetal image transmitted from an ultrasound diagnosis device through the communication unit;
- an ROI setting unit receiving a selection of a facial area in the fetal image according to a user input and setting the facial area as the ROI information;
- a growth information input unit receiving growth information including a pregnancy period and growth parameter for a pregnant woman;
- a terminal library DB storing a library in which components corresponding to a plurality of face shapes are defined; and
- a feedback unit receiving a selection of one or more components for facial portion of the fetus from a user and transmitting a codeword of a similar model to the image providing server.

7. A method for providing a model by an image providing server of a deep learning-based virtual reality 3D fetal model providing system according to claim 1, the method comprising:
- receiving a fetal image and ROI information from a mobile terminal;
- extracting per-facial portion features by inputting a fetal image corresponding to the ROI information to a deep learning model;
- generating a 3D fetal image reflecting the per-facial portion features through 3D modeling;
- providing the 3D fetal image to the mobile terminal;
- after providing the 3D fetal image to the mobile terminal, receiving a codeword for a similar model including one or more components per facial portion of the fetus selected by a user from the mobile terminal; and
- performing a machine learning process on the deep learning model using the codeword as training data.

* * * * *